US 11,147,579 B2

(12) United States Patent
Edwards et al.

(10) Patent No.: US 11,147,579 B2
(45) Date of Patent: Oct. 19, 2021

(54) METHODS OF RECIPROCATION IN A SURGICAL SHAVER

(71) Applicant: Gyrus ACMI, Inc., Southborough, MA (US)

(72) Inventors: Kevin Edwards, Olive Branch, MS (US); Ahmad Alsaffar, Bartlett, TN (US); Joel Willhite, Memphis, TN (US); David Church, Millington, TN (US); Daniel Goldberg, Germantown, TN (US)

(73) Assignee: Gyrus Acmi. Inc., Westborough, MA (US)

( * ) Notice: Subject to any disclaimer, the term of this patent is extended or adjusted under 35 U.S.C. 154(b) by 91 days.

(21) Appl. No.: 16/287,329

(22) Filed: Feb. 27, 2019

(65) Prior Publication Data

US 2020/0268402 A1 Aug. 27, 2020

(51) Int. Cl.
*A61B 17/32* (2006.01)

(52) U.S. Cl.
CPC .......... *A61B 17/32002* (2013.01); *A61B 2017/320028* (2013.01); *A61B 2017/320032* (2013.01)

(58) Field of Classification Search
CPC .......... A61B 17/32002; A61B 17/3207; A61B 17/320758; A61B 2017/320028; A61B 2017/320032; A61F 9/007; A61F 9/00763
See application file for complete search history.

(56) References Cited

U.S. PATENT DOCUMENTS

| 4,940,468 | A | 7/1990 | Petillo |
| 6,156,049 | A | 12/2000 | Lovato et al. |
| 6,258,111 | B1 | 7/2001 | Ross et al. |
| 6,342,061 | B1 | 1/2002 | Kauker et al. |
| 2002/0183851 | A1 | 12/2002 | Spiegelberg et al. |
| 2003/0009888 | A1 | 1/2003 | Marinkovich et al. |
| 2003/0083684 | A1 | 5/2003 | Cesarini et al. |
| 2005/0005458 | A1 | 1/2005 | Marinkovich et al. |
| 2007/0282344 | A1 | 12/2007 | Yedlicka et al. |
| 2009/0270893 | A1 | 10/2009 | Arcenio |
| 2011/0028898 | A1* | 2/2011 | Clark, III ............... A61B 90/03 604/151 |

(Continued)

FOREIGN PATENT DOCUMENTS

| EP | 3698737 A1 | 8/2020 |
| JP | 2005507703 | 3/2005 |
| JP | 2017529940 | 10/2017 |

OTHER PUBLICATIONS

Wikipedia contributors. "Scotch yoke." Wikipedia, The Free Encyclopedia. Wikipedia, The Free Encyclopedia, Apr. 1, 2019. Web. May 29, 2019, 3 pages.

(Continued)

*Primary Examiner* — Mohamed G Gabr
(74) *Attorney, Agent, or Firm* — Schwegman Lundberg & Woessner, P.A.

(57) ABSTRACT

Disclosed herein is a medical device. The medical device includes a blade tube section, a motor, and a cotch yoke or slotted link mechanism. The blade tube section includes an outer blade tube, an inner blade tube, and a cutting window at a distal end of the blade tube section. The motor is spaced from the blade tube section. The scotch yoke or slotted link mechanism is between the inner blade tube and the motor.

17 Claims, 5 Drawing Sheets

(56) References Cited

U.S. PATENT DOCUMENTS

| | | | |
|---|---|---|---|
| 2011/0247847 A1 | 10/2011 | Holmes et al. | |
| 2013/0211321 A1* | 8/2013 | Dubois | A61M 13/00 |
| | | | 604/26 |
| 2015/0090058 A1 | 4/2015 | Roschke et al. | |
| 2016/0331645 A1* | 11/2016 | Bagwell | A61M 3/0279 |
| 2017/0231654 A1 | 8/2017 | Cesarini et al. | |
| 2018/0146974 A1 | 5/2018 | Bjursten | |
| 2019/0070215 A1 | 3/2019 | Perry et al. | |
| 2020/0268400 A1 | 8/2020 | Edwards et al. | |
| 2020/0268401 A1 | 8/2020 | Edwards et al. | |
| 2020/0268946 A1 | 8/2020 | Wood | |
| 2020/0275944 A1 | 9/2020 | Goldberg et al. | |

OTHER PUBLICATIONS

Wikipedia contributors. "Driving wheel." Wikipedia, The Free Encyclopedia. Wikipedia, The Free Encyclopedia, Apr. 4, 2019. Web. May 22, 2019, 4 pages.

"U.S. Appl. No. 16/282,505, Non Final Office Action dated Oct. 28, 2020", 13 pgs.

"U.S. Appl. No. 16/286,748, Final Office Action dated Oct. 1, 2020", 12 pgs.

"U.S. Appl. No. 16/286,748, Non Final Office Action dated Jun. 16, 2020", 13 pgs.

"U.S. Appl. No. 16/286,748, Response filed Sep. 16, 2020 to Non Final Office Action dated Jun. 16, 2020", 13 pgs.

"U.S. Appl. No. 16/290,047, Final Office Action dated Oct. 20, 2020", 11 pgs.

"U.S. Appl. No. 16/290,047, Non Final Office Action dated Jun. 16, 2020", 13 pgs.

"U.S. Appl. No. 16/290,047, Response filed Sep. 16, 2020 to Non Final Office Action dated Jun. 16, 2020", 10 pgs.

"European Application Serial No. 20158861.3, Extended European Search Report dated Jun. 29, 2020", 7 pgs.

"U.S. Appl. No. 16/282,505, Response filed Jan. 28, 2021 Non Final Office Action dated Oct. 28, 2020", 11 pgs.

"U.S. Appl. No. 16/286,748, Response filed Jan. 4, 2021 to Final Office Action dated Oct. 1, 2020", 14 pgs.

"U.S. Appl. No. 16/290,047, Advisory Action dated Jan. 8, 2021", 3 pgs.

"U.S. Appl. No. 16/290,047, Response filed Jan. 15, 2021 to Advisory Action dated Jan. 8, 2021", 10 pgs.

"U.S. Appl. No. 16/290,047, Response filed Dec. 10, 2020 to Final Office Action dated Oct. 20, 2020", 9 pgs.

"European Application Serial No. 20158861.3, Response filed Feb. 25, 2021 to Extended European Search Report dated Jun. 29, 2020", 9 pgs.

"Japanese Application Serial No. 2020-28552, Notification of Reasons for Refusal dated Mar. 15, 2021", 14 pgs.

"U.S. Appl. No. 16/286,748, Non Final Office Action dated Apr. 27, 2021", 15 pgs.

"U.S. Appl. No. 16/282,505, Non Final Office Action dated Apr. 30, 2021", 11 pgs.

"U.S. Appl. No. 16/282,505, Response filed Jul. 30, 2021 to Non Final Office Action dated Apr. 30, 2021", 10 pgs.

"U.S. Appl. No. 16/286,748, Notice of Allowance dated Sep. 2, 2021", 5 pgs.

"U.S. Appl. No. 16/286,748, Response filed Jul. 27, 2021 to Non Final Office Action dated Apr. 27, 2021", 12 pgs.

"U.S. Appl. No. 16/290,047, Corrected Notice of Allowability dated Jun. 30, 2021", 3 pgs.

"U.S. Appl. No. 16/290,047, Corrected Notice of Allowability dated Jul. 12, 2021", 2 pgs.

"U.S. Appl. No. 16/290,047, Notice of Allowance dated Jun. 23, 21", 6 pgs.

"Japanese Application Serial No. 2020-28522, Response filed Jun. 15, 2021 to Office Action dated Mar. 15, 2021", w/ English Claims, 7 pgs.

* cited by examiner

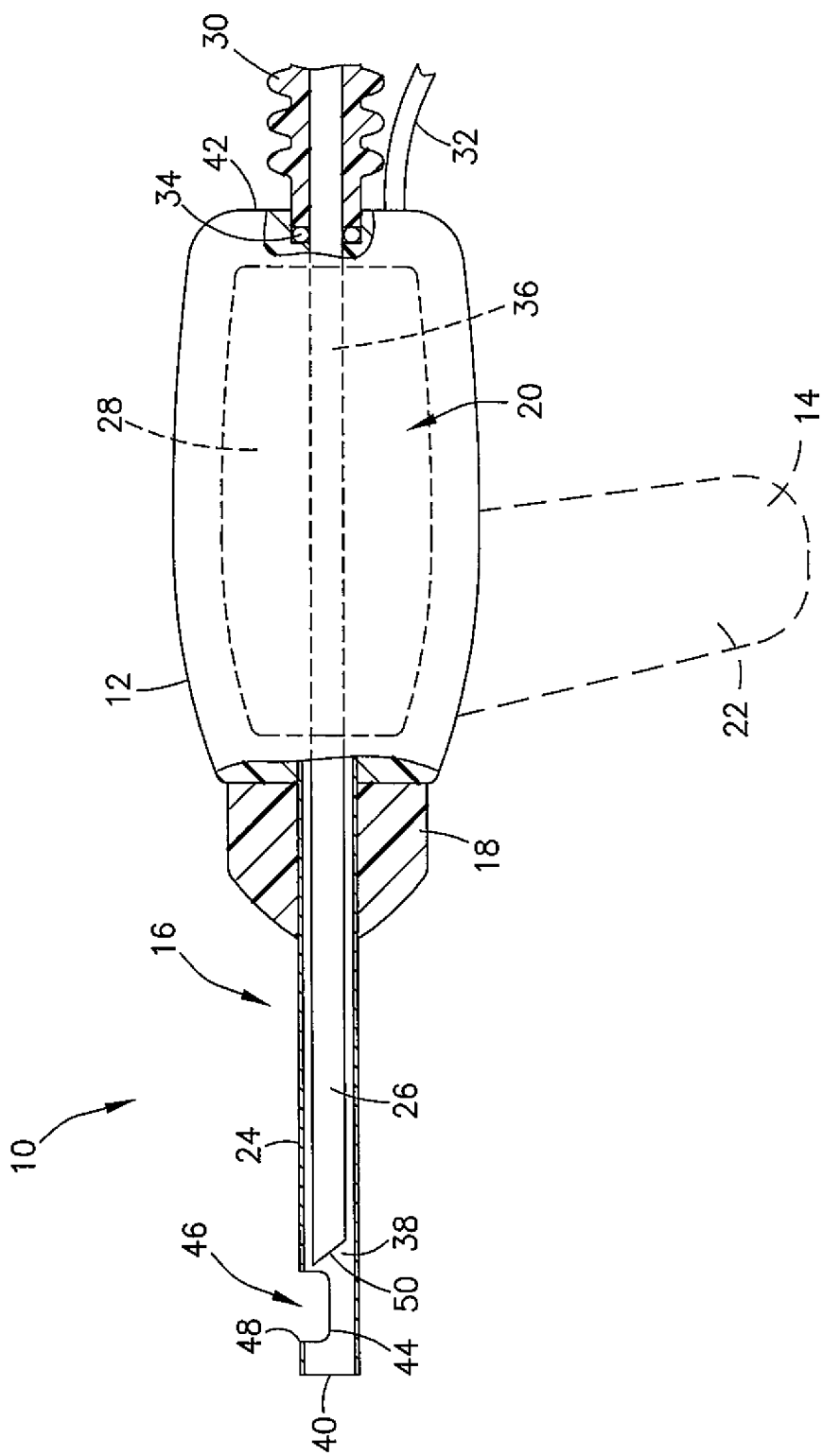

METHODS OF RECIPROCATION IN A SURGICAL SHAVER

BACKGROUND

Field of the Invention

The invention relates to a medical device and more specifically relates to methods of reciprocation for a surgical shaver device.

Brief Description of Prior Developments

Conventional surgical shavers generally use a rotational motor coupled with a parallel gear train to impart oscillatory motion on the shaver blades. However, using the oscillating motion to cut can tear and strip mucosa. Reciprocating blades, on the other hand, can create cleaner, more precise cuts.

Reciprocating surgical shavers exist in the market, however these devices generally use air pressure from a vacuum to drive the reciprocation, which can result in a weak cutting stroke and in turn make the device unable to cut through the tissue necessary to complete a procedure.

Accordingly, there is a need to provide improved and reliable medical device configurations having reciprocating blades.

SUMMARY

In accordance with one aspect of the invention, a medical device is disclosed. The medical device includes a blade tube section, a motor, and a cotch yoke or slotted link mechanism. The blade tube section includes an outer blade tube, an inner blade tube, and a cutting window at a distal end of the blade tube section. The motor is spaced from the blade tube section. The scotch yoke or slotted link mechanism is between the inner blade tube and the motor.

In accordance with another aspect of the invention, a medical device is disclosed. The medical device includes a blade tube section, a motor, a flywheel, and a slotted portion. The blade tube section includes an outer blade tube, and inner blade tube, and a cutting window at a distal end of the blade tube section. The flywheel has a pin. The flywheel is connected to the motor. The slotted portion is between the inner blade tube and the motor. The slotted portion is configured to receive the pin.

BRIEF DESCRIPTION OF THE DRAWINGS

The foregoing aspects and other features of the invention are explained in the following description, taken in connection with the accompanying drawings, wherein:

FIG. 1 is a side view of a medical device incorporating features of the invention;

DETAILED DESCRIPTION

Figure 3:
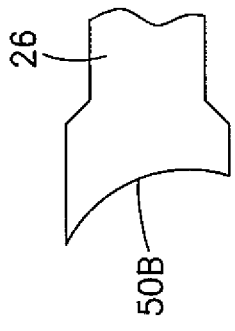
FIG. 3 is an alternate embodiment of a cutting tip used in the medical device shown in FIG. 1.
Figure 5:
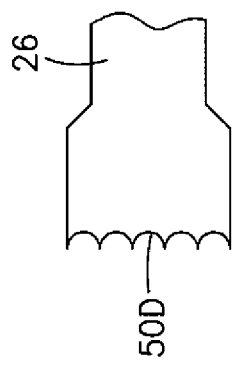
FIG. 5 is an alternate embodiment of a cutting tip used in the medical device shown in FIG. 1
Figure 2:
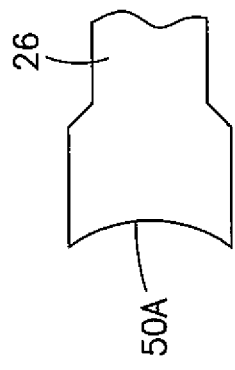
FIG. 2 is an alternate embodiment of a cutting tip used in the medical device shown in FIG. 1.
Figure 4:
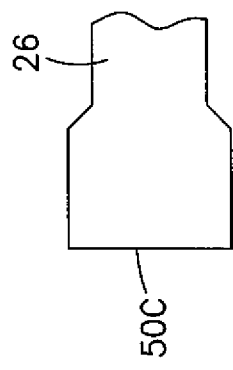
FIG. 4 is an alternate embodiment of a cutting tip used in the medical device shown in FIG. 1.

Referring to FIG. 1, there is shown a perspective view of a medical device 10 incorporating features of the invention. Although the invention will be described with reference to the exemplary embodiments shown in the drawings, it should be understood that the invention can be embodied in many alternate forms of embodiments. In addition, any suitable size, shape or type of elements or materials could be used.

According to various exemplary embodiments, the medical device 10 is generally configured for use in the removal of nasal polyps, sub-mucosal debulk of turbinates, and functional endoscopic sinus surgery (FESS).

The medical device 10, which may be a disposable debrider for example, comprises a housing 12 (which may have a pistol grip portion 14), a blade tube section 16, and a nosepiece 18. The nosepiece 18 may be a rotatable nosepiece and is between the housing 12 and the blade tube section 16. However, it should be noted that exemplary embodiments of the medical device may comprise any suitable configuration such as configurations having a nosecone coupled to an outer member (of the housing), or any other suitable curved or straight debrider configuration which may comprise an irrigation feature, for example. The blade tube section 16 of the device 10 can be configured with large and small shaver tubes, depending on anatomy and surgeon preference, and can also be adapted for bipolar or monopolar radio-frequency (RF) power. An external ESG (electrosurgical generator) may supply the RF power, for example.

The housing 12 comprises an interior cavity 20 sized and shaped to house actuation members of the device 10. Additionally, in some embodiments the optional pistol grip portion 14 may include an interior cavity 22 which can also be sized and shaped to house actuation members (or other hardware) of the device 10.

The blade tube section 16 comprises an outer blade tube 24 and an inner blade tube 26, and the medical device 10 further comprises a blade drive system 28 mounted within the cavity 20 (or mounted within the cavity 22) which is configured to drive the inner blade tube 26. It should be noted that in some embodiments, the blade tubes 24, 26 may comprise flexible and/or curved tubes.

Additionally, the medical device 10 comprises a connector 30 and a power cable 32. The connector (or suction connection) 30 is configured to connect to a suction tube or a vacuum source. The connector 30 includes a dynamic seal 34 mounted inside of the connector 30. The dynamic seal 34 is configured to provide a sealed interface between the connector 30 and an inner lumen 36 (via the outer surface of the inner blade tube 26) of the inner blade tube 26. The power cable 32 is configured to provide power to components(s) of the blade drive system 28.

The outer blade tube 24 is (rotatably or fixedly) mounted to the housing 12 and acts as a static member. For example, according to various exemplary embodiments, the nosepiece 18 can be mounted to the outer blade tube 24 and can optionally rotate the outer blade tube 24 independent of the housing 12. The inner blade tube 26 is slidably mounted inside the outer blade tube (such that the inner blade tube 26 is slideably mounted within a lumen 38 of the outer blade tube 24).

The inner blade tube 26 is configured to be forced distally [i.e. towards the distal end 40] or proximally [i.e. towards the proximal end 42] by the blade drive system 28. The outer blade tube 24 comprises an opening 44 proximate the distal end 40 which forms a cutting window 46 for the medical device 10. The cutting window 46 is formed by a cutting edge 48 of the outer blade tube (i.e. the distal edge of the opening 44) and a cutting tip 50 of the inner blade tube 26. The reciprocal motion of the inner blade tube 26 provides for the cutting tip 50 to reciprocate relative to the cutting edge 48 to perform tissue cuts (i.e. by bringing the cutting tip 50 into alignment and out of alignment with the opening 44 of the outer blade tube 24). In the embodiment shown in FIG. 1, the cutting edge 48 is at the cylindrical face portion of the cutting window 46. However in alternate embodiments, the cutting edge may be provided at any suitable location along the distal end 40.

It should be noted that although various exemplary embodiments of the invention have been described in connection with the cutting tip 50 comprising an angled straight edge configuration, alternate embodiments may comprise other suitable configurations. For example, FIGS. 2-5 illustrate alternate embodiments for the cutting tip 50 (see cutting tips 50A, 50B, 50C, 50D).

Figure 6:
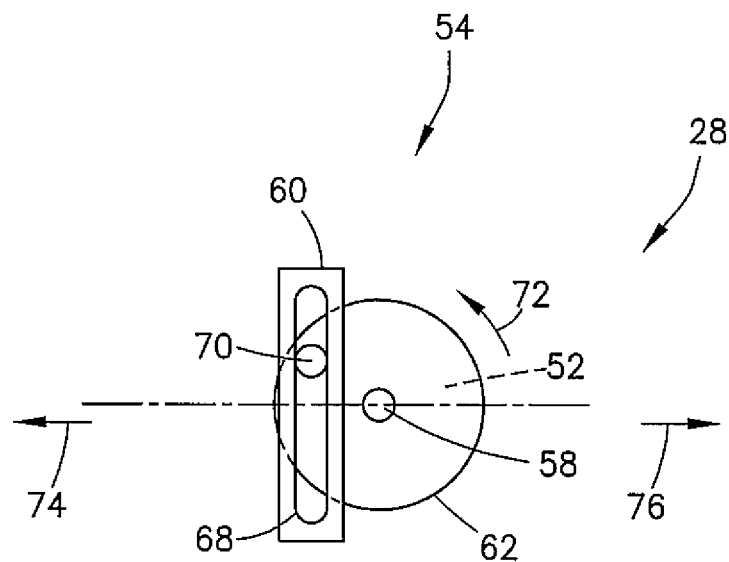
FIG. 6 is a top view of a blade drive system used in the medical device shown in FIG. 1.
Figure 7:
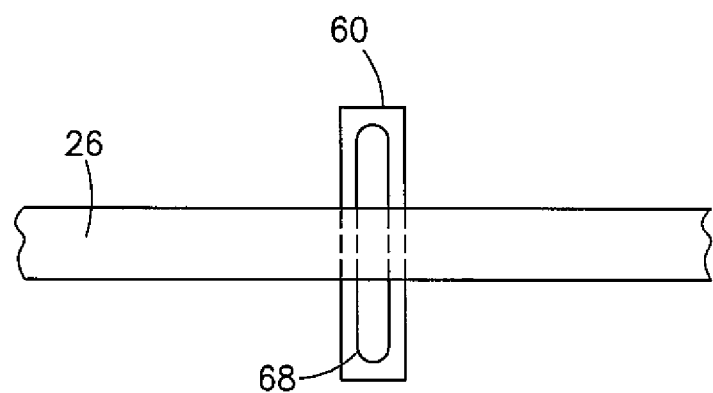
FIG. 7 is a partial view of the blade drive system shown in FIG. 6.
Figure 8:
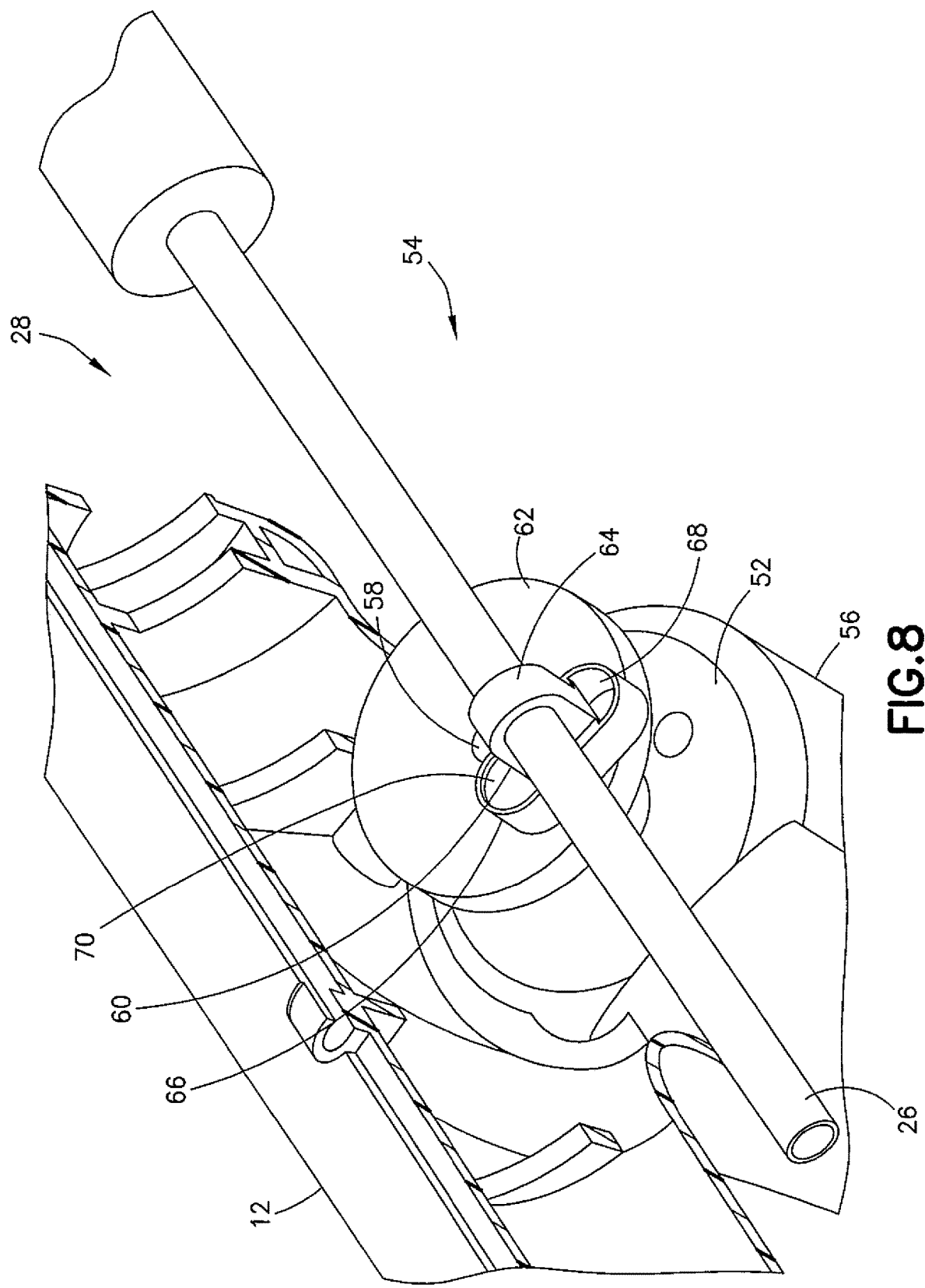
FIG. 8 is a perspective view of the blade drive system shown in FIG. 6.

Referring now also to FIG. 6-8, the blade drive system 28 comprises a motor 52 and a mechanical arrangement 54. The motor 52 is substantially perpendicular relative to a central axis of the blade tube section 16. The motor 52 generally comprises a motor housing 56 and a motor shaft 58 extending from the motor housing 56. The motor shaft 58 is configured to rotate when the motor 52 is electrically energized (by power cable 32). According to some embodiments, the motor 52, or at least a portion of the motor 52, may be disposed within the grip cavity 22. However, in alternate embodiments, any suitable location for the motor 52 may be provided (such as the housing cavity 20, for example).

The mechanical arrangement 54 comprises a collar 60 and a flywheel 62. The collar 60 comprises a flange section 64 and a yoke section 66. The flange section 64 is fixedly connected (or fixedly mounted) to the inner blade tube 26. The yoke section 66 comprises a slotted portion 68 having a general slot or racetrack shape. The flywheel comprises a pin 70 configured to be received in the slotted portion 68. The configuration of the yoke section 66 of the collar 60 and the pin 70 of the flywheel 62 forms a "scotch yoke" or a "slotted link mechanism" providing a reciprocating motion mechanism which converts the rotational motion of the flywheel 62 into linear motion of the collar 60 (and inner blade tube 26). For example, as the flywheel 62 rotates in direction 72, the pin 70 imparts a force on the collar 60 (in direction 74) while the pin 70 slides within the slotted portion 68. As the flywheel 62 continues to rotate, the collar 60 (and inner blade tube 26) reaches the end of the forward stroke, the continued rotation of the flywheel 62 begins to cause the pin 70 to impart a force on the collar 60 (in direction 76) while the pin 70 continues to slide within the slotted portion 68. As the flywheel 62 continues to rotate, the collar 60 (and inner blade tube 26) reaches the end of the reverse stroke and the continued rotation of the flywheel 62 begins to cause the pin 70 to impart a force on the collar 60 in the direction 76 to repeat the forward stroke.

Although the embodiment above has been described in connection with a 'counter clockwise' rotation of the flywheel, alternate embodiments may be provided with a 'clockwise rotation' of the flywheel to provide for reciprocal motion of the inner blade tube.

Technical effects of any one or more of the exemplary embodiments provide significant advantages over conventional configurations by providing greater force to the reciprocating blade than conventional air pressure-based devices can provide. A further technical effect of the various exemplary embodiments is providing a motor perpendicular from a central axis of the blade tube section.

Figure 9:
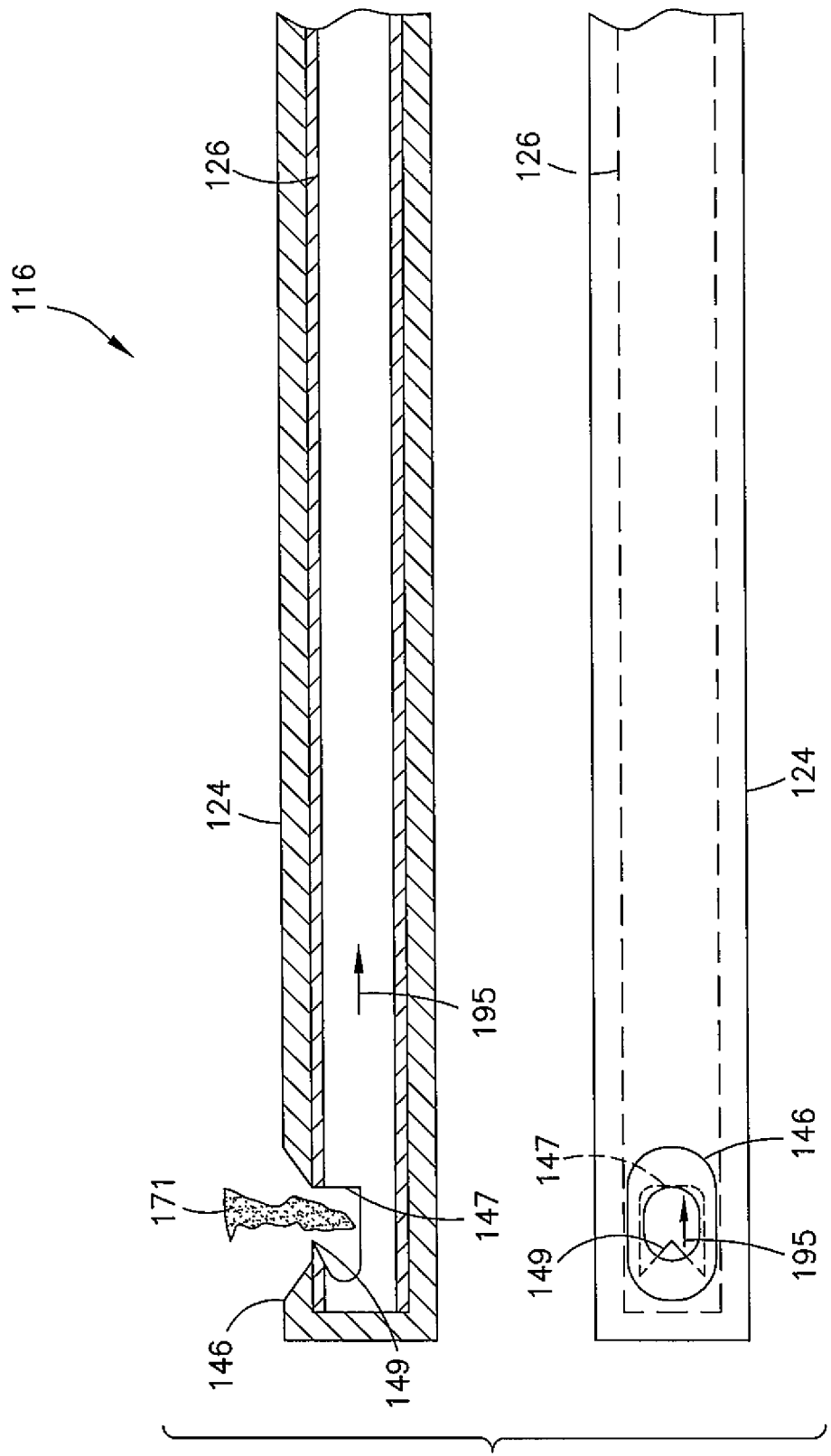
FIG. 9 is a section view and a top plan view of an alternate blade tube section used in the medical device shown in FIG. 1.

While various exemplary embodiments of the invention have been described in connection with a blade tube section 16 having a cutting edge 48 at the cutting window 46 of the outer blade tube 24, other configurations may be provided. For example, an alternate embodiment of a blade tube section 116 is shown in FIG. 9 (illustrating a cross-section view [top] and a top plan view [bottom]). Similar to the blade tube section 16, the blade tube section 116 comprises an outer blade tube 124 and an inner blade tube 126 configured to be driven by the blade drive system 28. However in this embodiment, the inner blade tube 126 comprises a cutting window 147 and a cutting edge 149. The cutting window 147 is configured to be aligned with the window 146 of the outer blade tube 124 such that the cutting is provided when tissue 171 extends through the windows 146, 147 and a backwards motion of the inner blade tube 126 (towards the proximate end [see arrow 195]) causes the cutting edge 149 to cut through the tissue 171.

In the embodiments described above the mechanical arrangement comprises the pin 70 on the flywheel 62 and the slotted portion 68 on the yoke section 66 of the collar. However, in alternate embodiments, the pin could be provided on the collar with a slotted section or portion (configured to receive the pin) on the flywheel. Additionally, in other alternate embodiments, any suitable combination of pin and slot features between the driving/flywheel and driven/collar components could be provided. It should further be noted that in various exemplary embodiments the diameter of the flywheel 62 (and related position of the drive pin 70) can be changed to create more/less drive force and more/less actuation stroke (this would have an inverse relationship [more stroke/less force, etc.]).

Below are provided further descriptions of various non-limiting, exemplary embodiments. The below-described exemplary embodiments may be practiced in conjunction with one or more other aspects or exemplary embodiments. That is, the exemplary embodiments of the invention, such as those described immediately below, may be implemented, practiced or utilized in any combination (e.g., any combination that is suitable, practicable and/or feasible) and are not limited only to those combinations described herein and/or included in the appended claims.

In one exemplary embodiment, a medical device comprising: a blade tube section comprising an outer blade tube, an inner blade tube, and a cutting window at a distal end of the blade tube section; a motor spaced from the blade tube section; and a scotch yoke or slotted link mechanism between the inner blade tube and the motor.

A medical device as above, further comprising a collar connected to the inner tube member.

A medical device as above, further comprising a flywheel, wherein the flywheel is connected to the motor.

A medical device as above, wherein flywheel comprises a pin.

A medical device as above, wherein the pin is configured to engage a portion of the collar.

A medical device as above, wherein the motor comprises a motor shaft, wherein the motor shaft is substantially perpendicular to the central axis of the blade tube section.

A medical device as above, further comprising a collar, wherein the collar is connected to the inner tube member, and wherein a yoke portion of the collar is configured to receive a pin rotated by the motor.

A medical device as above, wherein the inner blade tube is configured to reciprocate relative to the outer blade tube.

In another exemplary embodiment, a medical device comprising: a blade tube section comprising an outer blade tube, an inner blade tube, and a cutting window at a distal end of the blade tube section; a motor; a flywheel having a pin, wherein the flywheel is connected to the motor; and a slotted portion between the inner blade tube and the motor, wherein the slotted portion is configured to receive the pin.

A medical device as above, further comprising a collar fixedly connected to the inner tube member.

A medical device as above, wherein a mechanical arrangement is between the inner blade tube and the motor.

A medical device as above, wherein the mechanical arrangement comprises the flywheel.

A medical device as above, wherein flywheel comprises a pin.

A medical device as above, wherein the pin is configured to engage a portion of the collar.

A medical device as above, further comprising a collar, wherein the collar is connected to the inner tube member, and wherein a yoke section of the collar comprises the slotted portion.

A medical device as above, wherein the inner blade tube is configured to reciprocate relative to the outer blade tube.

A medical device as above, wherein the motor is substantially perpendicular relative to a central axis of the blade tube section.

It should be understood that components of the invention can be operationally coupled or connected and that any number or combination of intervening elements can exist (including no intervening elements). The connections can be direct or indirect and additionally there can merely be a functional relationship between components.

It should be understood that the foregoing description is only illustrative of the invention. Various alternatives and modifications can be devised by those skilled in the art without departing from the invention. Accordingly, the invention is intended to embrace all such alternatives, modifications and variances which fall within the scope of the appended claims.

What is claimed is:

1. A medical device comprising:
   a blade tube section comprising an outer blade tube, an inner blade tube, and a cutting window at a distal end of the blade tube section;
   a motor spaced from the blade tube section; and
   a mechanical arrangement comprising:
     a collar including a slotted yoke section and a flange section extending from a first side of the slotted yoke section, wherein the inner blade tube is fixedly mounted to the flange section; and
     a flywheel engageable with a second opposing side of the slotted yoke section.

2. The medical device of claim 1 wherein the flywheel, the slotted yoke section, and the inner blade tube are arranged in three parallel planes.

3. The medical device of claim 2 wherein the flywheel is connected to a rotatable motor shaft of the motor.

4. The medical device of claim 3 wherein the flywheel comprises a pin.

5. The medical device of claim 4 wherein the pin is configured to engage a slot in the slotted yoke section.

6. The medical device of claim 1 wherein the motor comprises a motor shaft, wherein the motor shaft is substantially perpendicular to the central axis of the blade tube section.

7. The medical device of claim 1 wherein the slotted yoke section of the collar is configured to receive a pin extending from the flywheel and rotated by the motor.

8. The medical device of claim 1 wherein the inner blade tube is configured to reciprocate relative to the outer blade tube.

9. A medical device comprising:
   a blade tube section comprising an outer blade tube, an inner blade tube, and a cutting window at a distal end of the blade tube section;
   a motor comprising a rotatable motor shaft;
   a flywheel having a pin, wherein the flywheel is directly connected to the motor shaft; and
   a slotted portion between the inner blade tube and the motor, wherein the slotted portion is configured to receive the pin.

10. The medical device of claim 9 further comprising a collar fixedly connected to the inner tube member.

11. The medical device of claim 10 wherein a mechanical arrangement is between the inner blade tube and the motor.

12. The medical device of claim 11 wherein the mechanical arrangement comprises the flywheel.

13. The medical device of claim 12 wherein the pin is configured to engage a portion of the collar.

14. The medical device of claim 9 further comprising a collar, wherein the collar is connected to the inner tube member, and wherein a yoke section of the collar comprises the slotted portion.

15. The medical device of claim 9 wherein the inner blade tube is configured to reciprocate relative to the outer blade tube.

16. The medical device of claim 9 wherein the motor is substantially perpendicular relative to a central axis of the blade tube section.

17. A medical device comprising:
   a blade tube section comprising an outer blade tube, an inner blade tube, and a cutting window at a distal end of the blade tube section;
   a motor comprising a rotatable motor shaft;
   a flywheel having a pin, wherein the flywheel is fixedly coupled to the motor shaft such that rotation of the motor shaft drives rotation of the flywheel; and
   a slotted portion between the inner blade tube and the motor, wherein the slotted portion is configured to receive the pin.

* * * * *